United States Patent
McManaway

(10) Patent No.: US 10,974,169 B2
(45) Date of Patent: Apr. 13, 2021

(54) AFFINITY CHROMATOGRAPHY DEVICES

(71) Applicant: W. L. Gore & Associates, Inc., Newark, DE (US)

(72) Inventor: Michael C. McManaway, Cecilton, MD (US)

(73) Assignee: W. L. Gore & Associates, Inc., Newark, DE (US)

(*) Notice: Subject to any disclaimer, the term of this patent is extended or adjusted under 35 U.S.C. 154(b) by 14 days.

(21) Appl. No.: 16/689,630

(22) Filed: Nov. 20, 2019

(65) Prior Publication Data

US 2020/0086232 A1 Mar. 19, 2020

Related U.S. Application Data

(62) Division of application No. 15/094,428, filed on Apr. 8, 2016, now Pat. No. 10,525,376.

(Continued)

(51) Int. Cl.
| | | |
|---|---|---|
| *B01D 15/38* | (2006.01) |
| *B01J 20/286* | (2006.01) |
| *B01J 20/28* | (2006.01) |
| *B01D 15/22* | (2006.01) |
| *B01D 69/14* | (2006.01) |

(Continued)

(52) U.S. Cl.
CPC ......... *B01D 15/3809* (2013.01); *B01D 15/22* (2013.01); *B01D 63/082* (2013.01); *B01D 63/10* (2013.01); *B01D 69/02* (2013.01); *B01D 69/148* (2013.01); *B01J 20/06* (2013.01); *B01J 20/103* (2013.01); *B01J 20/262* (2013.01); *B01J 20/286* (2013.01); *B01J 20/28035* (2013.01); *B01J 20/28052* (2013.01); *C07K 1/22* (2013.01); *C07K 16/00* (2013.01);

(Continued)

(58) Field of Classification Search
CPC ..................................................... B01D 69/148
See application file for complete search history.

(56) References Cited

U.S. PATENT DOCUMENTS

| | | |
|---|---|---|
| 3,953,566 A | 4/1976 | Gore |
| 4,113,912 A | 9/1978 | Okita et al. |

(Continued)

FOREIGN PATENT DOCUMENTS

| | | |
|---|---|---|
| DE | 10114537 | 10/2002 |
| EP | 64833 | 11/1982 |

(Continued)

*Primary Examiner* — Ryan B Huang
(74) *Attorney, Agent, or Firm* — Greenberg Traurig, LLP

(57) ABSTRACT

The present invention is directed to affinity chromatography devices that separate a targeted protein or antibody from an aqueous mixture containing the targeted protein or antibody. The chromatography device may contain a stacked membrane assembly or a wound membrane assembly. The membrane assemblies include at least one polymer membrane that contains therein inorganic particles. The polymer membrane and/or the inorganic particles have an affinity ligand bonded thereto. The affinity ligand may be a protein, an antibody, or a polysaccharide that reversibly binds to the targeted protein or antibody. The chromatography device may be repeatedly used and may be cleaned with a caustic solution between uses. The chromatography devices may have a dynamic binding capacity (DBC) of at least 30 mg/ml (or 0.07 micromol/ml) at 10% breakthrough at a residence time of 20 seconds or less.

19 Claims, 11 Drawing Sheets

Related U.S. Application Data

(60) Provisional application No. 62/194,620, filed on Jul. 20, 2015.

(51) Int. Cl.

| | | |
|---|---|---|
| *B01J 20/06* | (2006.01) | |
| *B01J 20/26* | (2006.01) | |
| *B01J 20/10* | (2006.01) | |
| *B01D 63/08* | (2006.01) | |
| *B01D 63/10* | (2006.01) | |
| *B01D 69/02* | (2006.01) | |
| *C07K 1/22* | (2006.01) | |
| *C07K 16/00* | (2006.01) | |

(52) U.S. Cl.
CPC ...... *B01D 2313/08* (2013.01); *B01D 2313/40* (2013.01); *B01D 2325/12* (2013.01)

(56) References Cited

U.S. PATENT DOCUMENTS

| | | |
|---|---|---|
| 4,895,806 A | 1/1990 | Le et al. |
| 5,183,545 A | 2/1993 | Branca et al. |
| 5,476,589 A | 5/1995 | Bacino |
| 5,708,044 A | 1/1998 | Branca |
| 5,897,955 A | 4/1999 | Drumheller |
| 5,904,848 A | 5/1999 | Wong et al. |
| 5,914,182 A | 6/1999 | Drumheller |
| 6,541,589 B1 | 4/2003 | Baillie |
| 7,045,365 B2 | 5/2006 | Coyne et al. |
| 7,306,729 B2 | 12/2007 | Bacino et al. |
| 7,531,611 B2 | 5/2009 | Sabol et al. |
| 8,591,932 B2 | 11/2013 | Cleek et al. |
| 8,637,144 B2 | 1/2014 | Ford |
| 8,658,707 B2 | 2/2014 | Xu et al. |
| 8,802,742 B2 | 8/2014 | Xu et al. |
| 9,139,669 B2 | 9/2015 | Xu et al. |
| 2005/0115890 A1 | 6/2005 | Demmer |
| 2005/0155890 A1 | 7/2005 | Manuel |
| 2011/0253616 A1 | 10/2011 | Childs et al. |
| 2014/0212612 A1 | 7/2014 | Sbriglia |
| 2016/0031130 A1 | 2/2016 | Sbriglia |
| 2016/0032069 A1 | 2/2016 | Sbriglia |
| 2016/0032701 A1 | 2/2016 | Sbriglia |

FOREIGN PATENT DOCUMENTS

| | | |
|---|---|---|
| EP | 64833 A3 | 11/1982 |
| EP | 0263934 | 4/1988 |
| EP | 0323055 | 7/1989 |
| EP | 0323055 A2 | 7/1989 |
| EP | 0352917 A2 | 1/1990 |
| EP | 2014359 A1 | 1/2009 |
| JP | 1982501466 | 3/1982 |
| JP | 1988072699 | 8/1987 |
| JP | 63216469 | 9/1988 |
| JP | 1990071837 | 7/1989 |
| JP | 1989-120903 U | 8/1989 |
| JP | 1120903 | 8/1989 |
| JP | 1209363 | 8/1989 |
| JP | 02-071837 A | 3/1990 |
| JP | H04232852 A | 8/1992 |
| JP | 6308109 | 11/1994 |
| JP | 6308109 A | 11/1994 |
| JP | H06308109 A | 11/1994 |
| JP | H07500363 A | 1/1995 |
| JP | 2008514424 | 5/2008 |
| JP | 2008514424 A | 5/2008 |
| JP | 2013235011 | 11/2013 |
| JP | 2018-502811 | 12/2018 |
| WO | WO-82/00774 | 3/1982 |
| WO | WO-91/10492 | 7/1991 |
| WO | WO-97/0288998 | 8/1997 |
| WO | WO-2015/052465 A1 | 4/2015 |

AFFINITY CHROMATOGRAPHY DEVICES

This application is a Divisional Application under 35 U.S.C. § 121 of U.S. patent application Ser. No. 15/094,428, filed on Apr. 8, 2016, which claims priority to U.S. Provisional Patent Application No. 62/194,620 filed on Jul. 20, 2015, the entire contents of which are incorporated by reference in their respective entireties.

FIELD

The present disclosure relates generally to affinity chromatography, and more specifically to chromatography devices containing a multilayered membrane assembly that enables the separation of a targeted protein or antibody from an aqueous mixture.

BACKGROUND

Chromatographic methods generally are used to separate and/or purify molecules of interest such as proteins, nucleic acids, and polysacchandes from a mixture. Affinity chromatography specifically involves passing the mixture over a matrix having a ligand specific (i.e. a specific binding partner) for the molecule of interest bound to it. Upon contacting the ligand, the molecule of interest is bound to the matrix and is therefore retained from the mixture. Affinity chromatography provides certain advantages over other types of chromatography. For example, affinity chromatography provides a purification method that can isolate a target protein from a mixture of the target protein and other biomolecules in a single step in high yield.

Despite the advantages of current affinity chromatography devices, there exists a need in the art for a chromatography device that can be used at shorter residence times than conventional devices while providing the same binding capacity or better binding capacities than current offerings and that is re-useable.

SUMMARY

One embodiment relates to an affinity chromatography device that includes a housing, a first flow distributor and a second flow distributor positioned at opposing ends of the housing, an inlet to permit fluid flow into the housing, an outlet to permit fluid flow out of the housing, and a stacked membrane assembly disposed within the housing. The stacked membrane assembly includes two or more polymer membranes that contain therein first inorganic particles having a first nominal particle size and second inorganic particles having a second nominal particle size. At least one of the polymer membranes, the first inorganic particles, and the second inorganic particles has covalently bonded thereto an affinity ligand that reversibly binds to a targeted protein or antibody. In one or more embodiment, the first and second inorganic particles are of the same particle type. The inorganic particles have a nominal particle size that may be about 5 microns, about 10 microns, about 15 microns, about 20 microns, about 25 microns and combinations thereof.

Another embodiment relates to an affinity chromatography device that includes a housing, a first flow distributor and a second flow distributor positioned at opposing ends of the housing, an inlet to permit fluid flow into the housing, an outlet to permit fluid flow out of the housing, and a wound membrane assembly disposed within the housing. The housing may be a cylindrical housing. The wound membrane assembly includes at least one polymer membrane that contains therein first inorganic particles having a first nominal particle size and second inorganic particles having a second nominal particle size. At least one of the polymer membrane, the first inorganic particles, and the second inorganic particles has covalently bonded thereto an affinity ligand that reversibly binds to a targeted protein or antibody. In one or more embodiment, the first and second inorganic particles are of the same particle type. The inorganic particles have a nominal particle size that may be about 5 microns, about 10 microns, about 15 microns, about 20 microns, about 25 microns and combinations thereof.

Yet another embodiment relates to an affinity chromatography device that includes a housing, a first flow distributor and a second flow distributor positioned at opposing ends of the housing, an inlet to permit fluid flow into the housing, an outlet to permit fluid flow out of the housing, and a stacked membrane assembly disposed within the housing. The stacked membrane assembly includes two or more polymer membranes that contain therein inorganic particles having a nominal particle size. At least one of the polymer membranes and the inorganic particles has covalently bonded thereto an affinity ligand that reversibly binds to a targeted protein or antibody. In at least one embodiment, the polymer membranes are of the same polymer type.

A further embodiment relates to an affinity chromatography device that includes a housing, a first flow distributor and a second flow distributor positioned at opposing ends of the housing, an inlet to permit fluid flow into the housing, an outlet to permit fluid flow out of the housing, and a wound membrane assembly. The wound membrane assembly includes a single polymer membrane containing therein inorganic particles having a single nominal particle size. At least one of the polymer membrane and the inorganic particles has covalently bonded thereto an affinity ligand that reversibly binds to a targeted protein or antibody. The inorganic particles have a nominal particle size that may be about 5 microns, about 10 microns, about 15 microns, about 20 microns, about 25 microns and combinations thereof. In one embodiment, the polymer membrane is a polytetrafluoroethylene membrane.

Another embodiment relates to an affinity chromatography device that includes a housing, a first flow distributor and a second flow distributor positioned at opposing ends of the housing, an inlet to permit fluid flow into the housing, an outlet to permit fluid flow out of the housing, and a stacked membrane assembly disposed within the housing. The stacked membrane assembly includes a first polymer membrane containing therein first inorganic particles having a first nominal particle size and a second polymer membrane containing therein second inorganic particles having a second nominal particle size. At least one of the first polymer membrane, the second polymer membrane, and the inorganic particles has covalently bonded thereto an affinity ligand that reversibly binds to a targeted protein or antibody.

A further embodiment relates to a method for separating a target protein or antibody from an aqueous mixture that includes passing an aqueous mixture through a chromatography device that includes a housing, a first flow distributor and a second flow distributor positioned at opposing ends of the housing, an inlet to permit fluid flow into the housing, an outlet to permit fluid flow out of the housing, and a stacked membrane assembly disposed within the housing. The membrane assembly includes two or more polymer membranes that contain therein first inorganic particles having a first nominal particle size second inorganic particles having a second nominal particle size. At least one of the polymer membranes, the first inorganic particles, and the second inorganic particles has covalently bonded thereto an affinity ligand that reversibly binds to a targeted protein or antibody. In one or more embodiment, the first and second inorganic particles are of the same particle type.

Yet another embodiment relates to a method for separating a target protein or antibody from an aqueous mixture that includes passing an aqueous mixture through a chromatography device that includes a housing, a first flow distributor and a second flow distributor positioned at opposing ends of the housing, an inlet to permit fluid flow into the housing, an outlet to permit fluid flow out of the housing, and a wound membrane assembly disposed within the housing. The wound membrane assembly includes at least one polymer membrane that contains therein first inorganic particles having a first nominal particle size and second inorganic particles having a second nominal particle size. At least one of the polymer membrane, the first inorganic particles, and the second inorganic particles has covalently bonded thereto an affinity ligand that reversibly binds to a targeted protein or antibody. In one or more embodiment, the first and second inorganic particles are of the same particle type.

Another embodiment relates to a multi-well affinity chromatography device that includes a plurality of wells and a stacked membrane assembly disposed within at least one of the wells. The stacked membrane assembly includes two or more polymer membranes that contain therein first inorganic particles having a first nominal particle size and second inorganic particles having a second nominal particle size. At least one of the polymer membranes, the first inorganic particles, and the second inorganic particles has covalently bonded thereto an affinity ligand that reversibly binds to a targeted protein or antibody. In one or more embodiment, the first and second inorganic particles are of the same particle type.

Yet another embodiment relates to a multi-well affinity chromatography device that includes a plurality of wells and a wound membrane assembly disposed within at least one of the wells. The wound membrane assembly includes at least one polymer membrane that contains therein first inorganic particles having a first nominal particle size and second inorganic particles having a second nominal particle size. At least one of the polymer membrane, the first inorganic particles, and the second inorganic particles has covalently bonded thereto an affinity ligand that reversibly binds to a targeted protein or antibody. In one or more embodiment, the first and second inorganic particles are of the same particle type.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
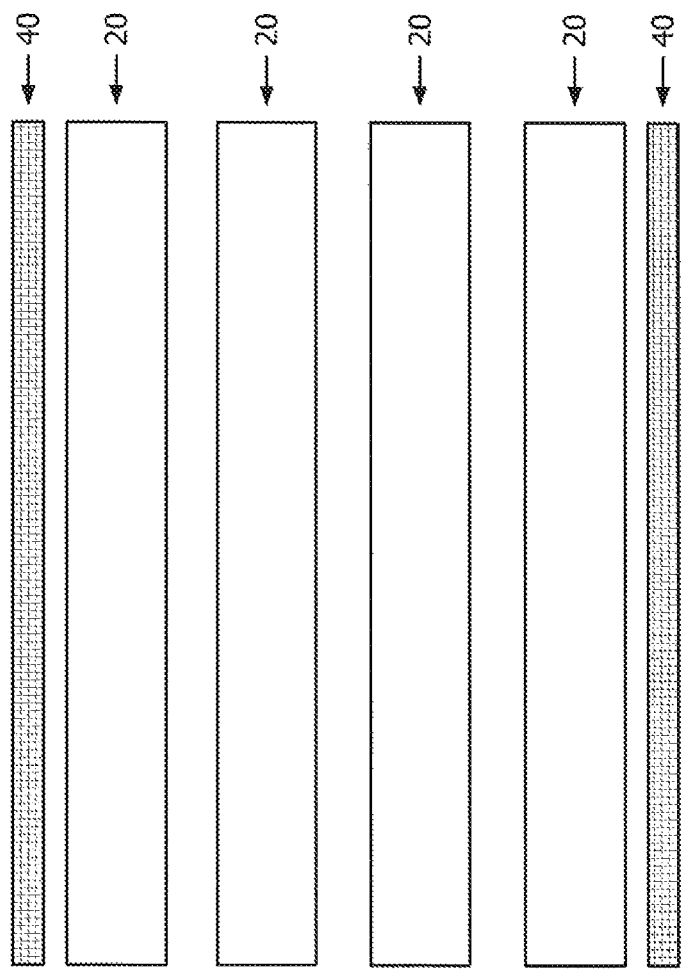
FIG. 1 is an exploded view of a stacked membrane assembly containing polymer membranes having therein inorganic particles according to at least one embodiment.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting. It is to be understood that, as used herein, the term "on" is meant to denote an element, such as a polymer membrane, is directly on another element or intervening elements may also be present.

The present invention is directed to affinity chromatography devices that separate a targeted protein or antibody from an aqueous mixture containing the targeted protein or antibody. The chromatography device contains a membrane assembly that includes at least one polymer membrane, such as a fluoropolymer membrane, that contains therein inorganic particles. An affinity ligand may be bonded to the inorganic particles and/or to the polymer membrane. The chromatography device may be repeatedly used and may be cleaned with a caustic solution between uses. In addition, the chromatography devices have a dynamic binding capacity (DBC) of at least 30 mg/ml at 10% breakthrough at a residence time of 20 seconds or less in devices where an Fc binding protein is the affinity ligand. In chromatography devices where an antibody, a non-Fc binding protein, or a polysaccharide is the affinity ligand, the chromatography devices have a dynamic binding capacity (DBC) of at least 0.07 micromol/ml at 10% breakthrough.

The membrane assemblies described herein include at least one polymer membrane that contains therein inorganic particles. The polymer membranes may contain from about 20 mass % to about 95 mass %, from about 35 mass % to about 90 mass %, or from about 50 mass % to about 85 mass % inorganic particles. Non-limiting examples of suitable inorganic particles include silica, zeolites, hydroxyapatite, metal oxides, and combinations thereof. The inorganic particles may have a nominal particle size of about 0.1 microns, about 0.5 microns, about 1 micron, about 5 microns, about 10 microns, about 15 microns, about 20 microns, or about 25 microns or more. Additionally, the inorganic particles may be either solid or porous and may have a variety of sizes and shapes. Further, the inorganic particles may be monodisperse or polydisperse.

In an exemplary embodiment, the affinity ligand is covalently bonded to the inorganic particles. In another embodiment, the affinity ligand is covalently bonded to the polymer membrane. In a further embodiment, the affinity ligand may be bound to both the polymer membrane and the inorganic particle(s). The affinity ligand may be a protein, antibody, or polysaccharide that reversibly binds to a targeted protein or antibody. In one embodiment, the affinity ligand is a protein that reversibly binds, for example, to an Fc region of an antibody, an antibody fragment, an Fc fusion protein, or an antibody/drug conjugate. In another embodiment, the affinity ligand is an antibody, Protein L, or a polysaccharide that reversibly binds to a protein or a protein fragment to which it is specific. Exemplary affinity ligands for use in the affinity chromatography device include, but are not limited to, Protein A, Protein G, Protein L, human Fc receptor protein, antibodies that specifically bind to other proteins, and heparin. The affinity ligand may be native, recombinant, or synthetic. In yet another embodiment, the affinity ligand is a metal affinity ligand that reversibly binds to His-Tagged Proteins.

In one embodiment, the membrane assembly includes at least one polymer membrane that contains therein inorganic particles where the polymer membranes are positioned in a stacked or layered configuration to form a stacked membrane assembly. The term "stacked membrane assembly" is meant to denote a chromatographic article that contains at least two polymer membranes positioned such that one polymer membrane is on another polymer membrane. The polymer membranes may be positioned in a stacked configuration by simply laying the membranes on top of each other. FIG. 1 depicts one exemplary orientation of a stacked membrane assembly 10 that includes polymer membranes 20 containing therein inorganic particles having a nominal particle size. It is to be appreciated that the inorganic particles are described herein with respect to nominal particle size to take into consideration the variability of sizes and shapes of the inorganic particles. The arrow 5 depicts the direction of fluid flow through the membrane assembly 10.

In one exemplary embodiment, the polymer membrane 20 contains a single type of inorganic particle having a single nominal particle size. For instance, the polymer membrane 20 may contain therein porous silica particles that have a nominal particle size of about 20 microns. It is to be understood that the term "silica" as used herein is meant to denote silicon dioxide that does not contain any measurable amount of boron or contains no boron as measured by x-ray photoelectron spectroscopy (XPS).

Alternatively, the polymer membrane 20 may contain more than one type of inorganic particle and/or more than one nominal particle size within the polymer membrane 20. In other words, the polymer membrane 20 may contain at least first inorganic particles and second inorganic particles where the first inorganic particles are different from the second inorganic particles in nominal particle size and/or type. For example, the polymer membrane 20 may include a mixture of a first particle size (e.g., 20 microns) and a second particle size (e.g., 10 microns) of the same or different inorganic particle (e.g., porous silica). The mixture of inorganic particles within the polymer membrane 20 may be any mixture, such as a 50/50 blend, a 30/70 blend, a 60/40 blend, a 25/75, or a 20/80 blend.

Figure 2:
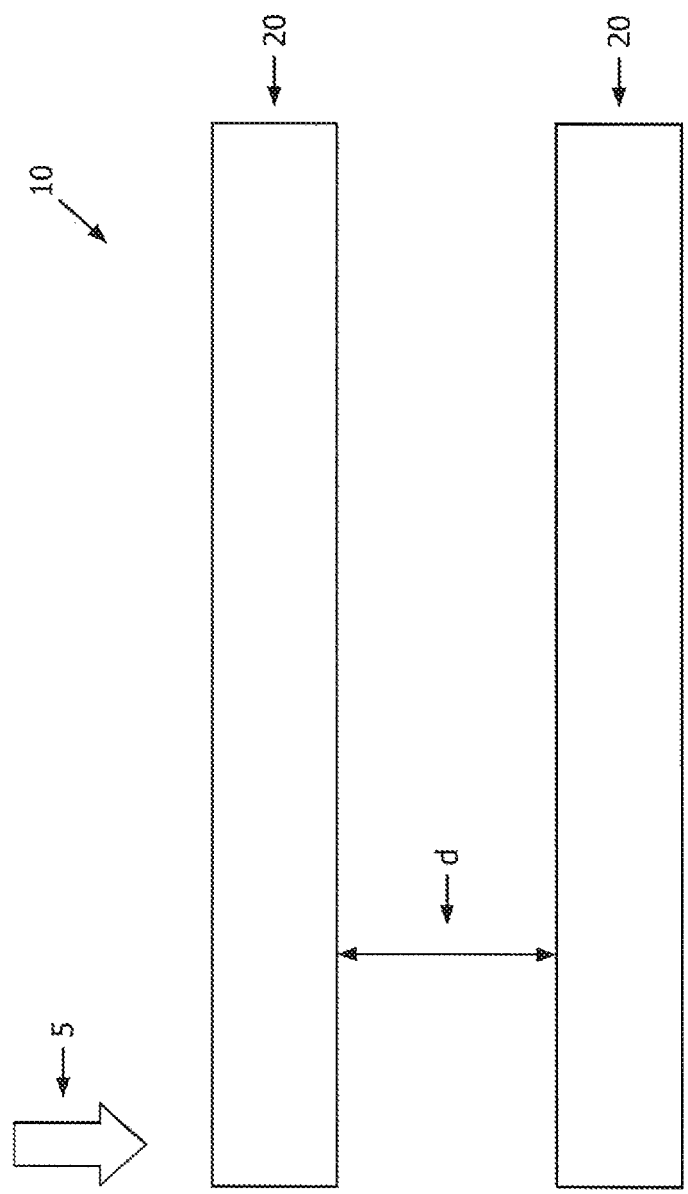
FIG. 2 is a schematic illustration of layers of polymer membranes within a membrane assembly in accordance with an exemplary embodiment.

The polymer membranes 20 in the stacked membrane assembly 10 may be positioned such the first and second polymer membranes are separated from each other by a distance (d), as shown schematically in FIG. 2. The distance d may range from about 0 microns to about 50 microns, from about 0 microns to about 25 microns, from about 0 microns to about 10 microns, or from about 0 microns to about 5 microns. In some embodiments, the distance d is zero or substantially zero microns (i.e., less than or equal to 0.1 microns). The distance may also be less than about 50 microns, less than about 25 microns, less than about 10 microns, less than about 5 microns, less than about 1 micron, or zero microns.

Figure 3:
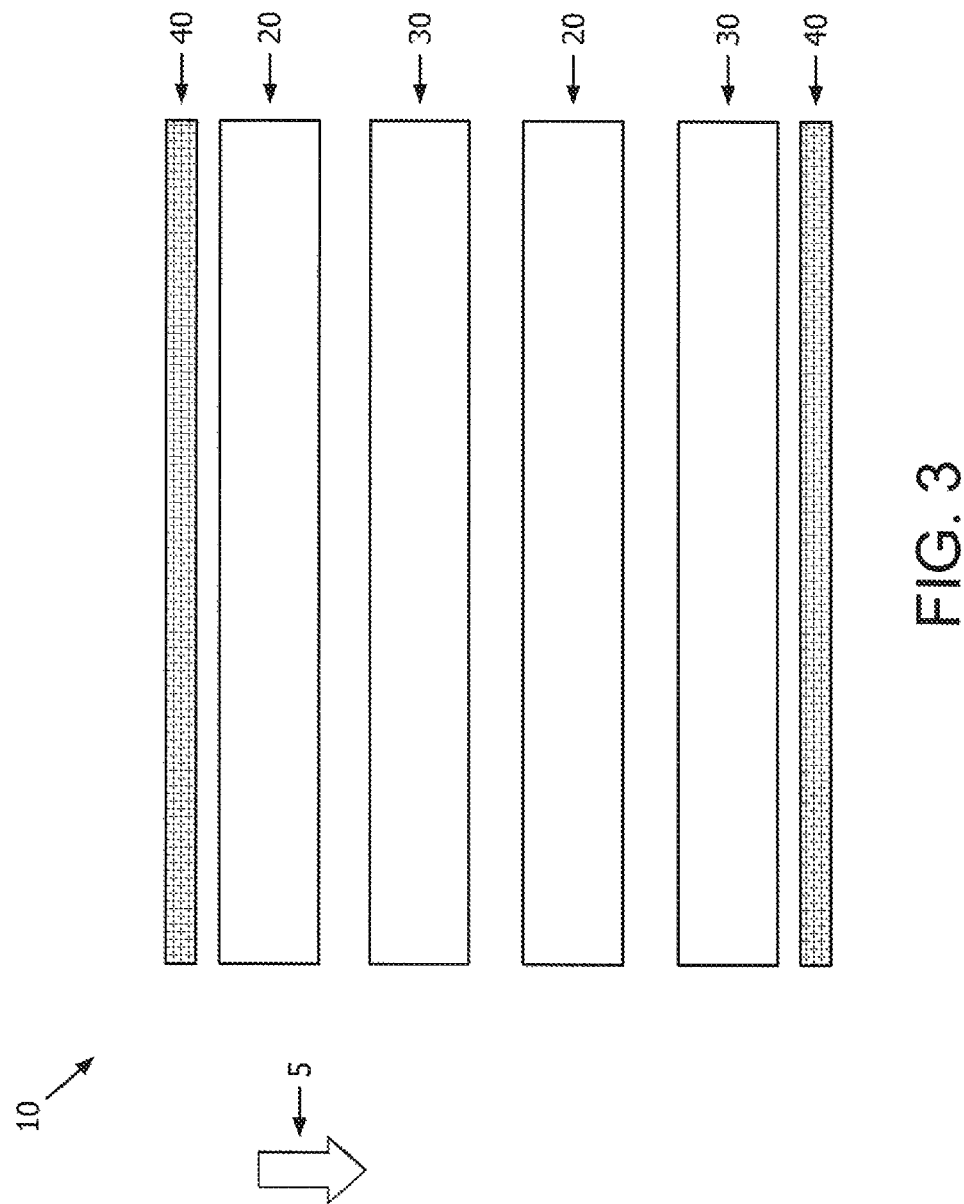
FIG. 3 is an exploded view of polymer membranes having an alternating configuration within a stacked membrane assembly according to at least one exemplary embodiment.

In another embodiment depicted generally in FIG. 3, the stacked membrane assembly 10 includes a first polymer membrane 20 containing inorganic particles having a first nominal particle size and a second polymer membrane 30 containing inorganic particles having a second nominal particle size. The first polymer membrane 20 and the second polymer membrane 30 may be stacked in an alternating fashion to form the membrane assembly 10, such as is exemplified in FIG. 3. The first and second polymer membranes 20, 30 may alternatively be stacked in a non-alternating configuration. For instance, multiple first membranes 20 may be positioned on multiple second membranes 30. In another embodiment, multiple polymer membranes 20 may be alternatively stacked with multiple second membranes 30 to form the membrane assembly 10. Also, a plurality of first polymer membranes 20 may be alternatively layered on a single (or lesser or greater number of) second polymer membrane 30, and vice versa, to form a stacked membrane assembly 10. Additional polymer membranes containing inorganic particles may also be present in the membrane assembly.

The polymer membranes 20, 30 may be positioned in a stacked configuration by simply laying the membranes on top of each other. Alternatively, the polymer membranes 20, 30 may be stacked and subsequently laminated together with heat and/or pressure or other conventional methods. Embodiments employing two polymer membranes that are co-expanded to produce a composite membrane assembly is also considered to be within the purview of the invention. Such a composite membrane assembly may contain two (or more) layers of polymer membranes that may be co-extruded or integrated together. In exemplary embodiments, the first polymer membrane 20 and second polymer membrane 30 are in a stacked configuration and the distance between the first and second polymer membranes is zero or substantially zero.

In another embodiment, the inorganic particles are of the same type in both the first polymer membrane 20 and the second polymer membrane 30. For example, both polymer membranes 20, 30 may include porous silica particles. Alternatively, the inorganic particles in the first and second membranes may have different nominal particle sizes. In some embodiments, the inorganic particles in the first polymer membrane 20 and the second polymer membrane 30 have the same nominal particle size or substantially the same nominal particle size.

In a further embodiment, the first and/or second polymer membranes 20, 30 may contain more than one type of inorganic particle within the polymer membrane. In other words, the first polymer membrane 20 and/or the second polymer membrane 30 may contain at least a first inorganic particle and a second inorganic particle where the first inorganic particle is different from the second inorganic particle in nominal particle size and/or type. For example, the polymer membrane(s) 20, 30 may include a 50/50 mixture of a first nominal particle size (e.g., 20 microns) and a second nominal particle size (e.g., 10 microns) of the same or different inorganic particle. The mixture of inorganic particles within the first and/or second polymer membrane 20, 30 may be any mixture, such as, for example, a 50/50 blend, a 30/70 blend, a 60/40 blend, a 25/75, or a 20/80 blend. In at least one embodiment, the membrane assembly 10 includes first and second polymer membranes 20, 30 that are formed of the same polymer membrane (e.g., PTFE membranes) and the inorganic particles are the same (e.g., porous silica particles) but the inorganic particles have different nominal particle sizes (e.g., 20 micron silica particles in one polymer membrane and 10 micron silica particles in the other polymer membrane).

The polymer membranes 20, 30 discussed herein may be formed of the same or different polymer(s). In one or more exemplary embodiment, at least one of the polymer membranes is a fluoropolymer membrane. It is to be appreciated that one, or more than one, fluoropolymer membrane may form or form part of the stacked membrane assembly 10. The fluoropolymer membranes may be derived from the same fluoropolymer source, from different sources, or a combination thereof. In at least one exemplary embodiment, the fluoropolymer membrane is a polytetrafluoroethylene (PTFE) membrane or an expanded polytetrafluoroethylene (ePTFE) membrane. Expanded polytetrafluoroethylene (ePTFE) membranes prepared in accordance with the methods described in U.S. Pat. No. 7,306,729 to Bacino et al., U.S. Pat. No. 3,953,566 to Gore, U.S. Pat. No. 5,476,589 to Bacino, or U.S. Pat. No. 5,183,545 to Branca et al. may be used herein. Further, the fluoropolymer membrane may be rendered hydrophilic (e.g., water-wettable) using known methods in the art, such as, but not limited to, the method disclosed in U.S. Pat. No. 4,113,912 to Okita, et al. A coating that effectively binds to a ligand, such as described in U.S. Pat. No. 5,897,955 to Drumheller, U.S. Pat. No. 5,914,182 to Drumheller, or U.S. Pat. No. 8,591,932 to Drumheller may be applied to the polymer membrane.

The fluoropolymer membrane may also include an polymer material comprising a functional tetrafluoroethylene (TFE) copolymer material where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. A functional TFE copolymer material may be prepared, for example, according to the methods described in U.S. Pat. No. 9,139,707 to Xu et al. or U.S. Pat. No. 8,658,707 to Xu et al.

It is to be understood that throughout the application, the term "PTFE" is utilized herein for convenience and is meant to include not only polytetrafluoroethylene, but also expanded PTFE, expanded modified PTFE, and expanded copolymers of PTFE, such as described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu, et al.

In one or more exemplary embodiment, the polymer membrane may be formed with one or more non-fluoropolymer materials, such as, but not limited to ultra-high molecular weight polyethylene as taught in U.S. Patent Publication No. 2014/0212612 to Sbriglia, polyparaxylylene as taught in U.S. Provisional Application No. 62/030,419 to Sbriglia, VDF-co-(TFE or TrFE) polymers as taught in U.S. Provisional Patent Application No. 62/030,442 to Sbriglia, alternating poly(ethylene tetrafluoroethylene polymers as taught in U.S. Provisional Patent Application No. 62/030, 448 to Sbriglia. Also, the polymer membrane may be, for example, a polyolefin membrane (e.g. polypropylene membrane), an organic membrane (e.g., a cellulose-based membrane), a structured hydrogel membrane, or an agarose membrane.

The total number of polymer membranes present in the stacked membrane assembly 10 is not particularly limited, and depends on the desired end use and/or desired mass transit flow within the membrane assembly. The stacked membrane assembly may include 2, 3, 4, 5, 6, 7, 8, 9, 10, 11, 12, 13, 14, 15, 16, 17, 18, 19, or 20 (or more) total polymer membranes. It is to be appreciated that hundreds or even thousands of polymer membranes may be present in the stacked membrane assembly 10.

In addition, the polymer membranes present in the stacked membrane assembly 10 may have a thickness from about 1 micron to about 10,000 microns, from about 100 microns to about 5,000 microns, from about 500 microns to about 3,000 microns, or from about 650 microns to about 1,000 microns. As used herein, the term "thickness" is the direction of the polymer membrane normal to the length area of the polymer membrane.

The chromatography device 100 may further include a porous frit 40 positioned at the top and/or bottom of the membrane assembly 10. The porous frit 40, housing 50, and flow distributors 60, 70 may be formed of a thermoplastic polymer such as polypropylene, polyethylene, or other polyolefins. Alternatively, the porous frit 40 may be formed of an inorganic or metallic material, so long as the frit 40 does not hinder the operation of the chromatography device.

Figure 4:
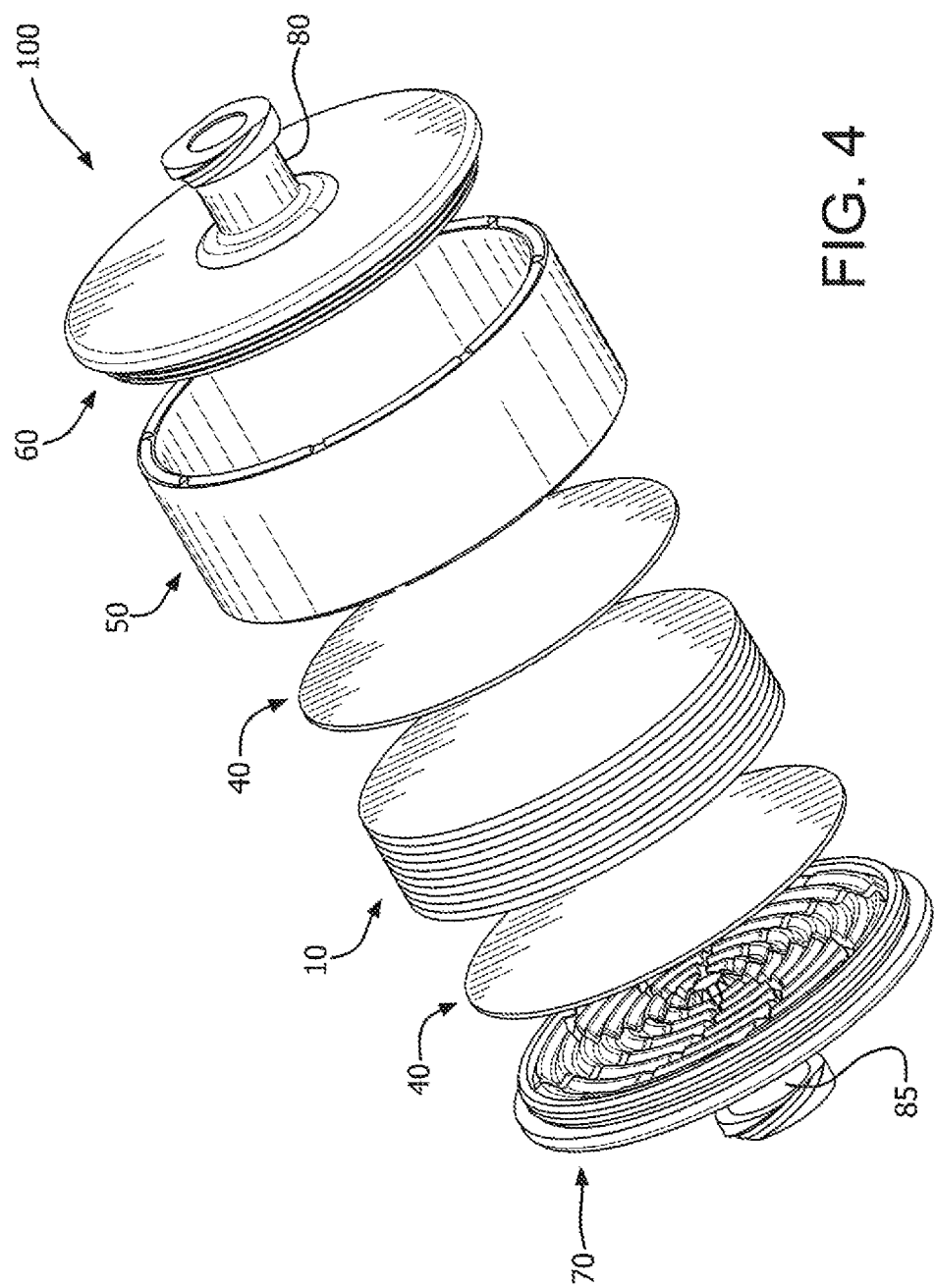
FIG. 4 is an exploded view of a chromatography device containing a stacked membrane assembly in accordance with an exemplary embodiment.
Figure 5:
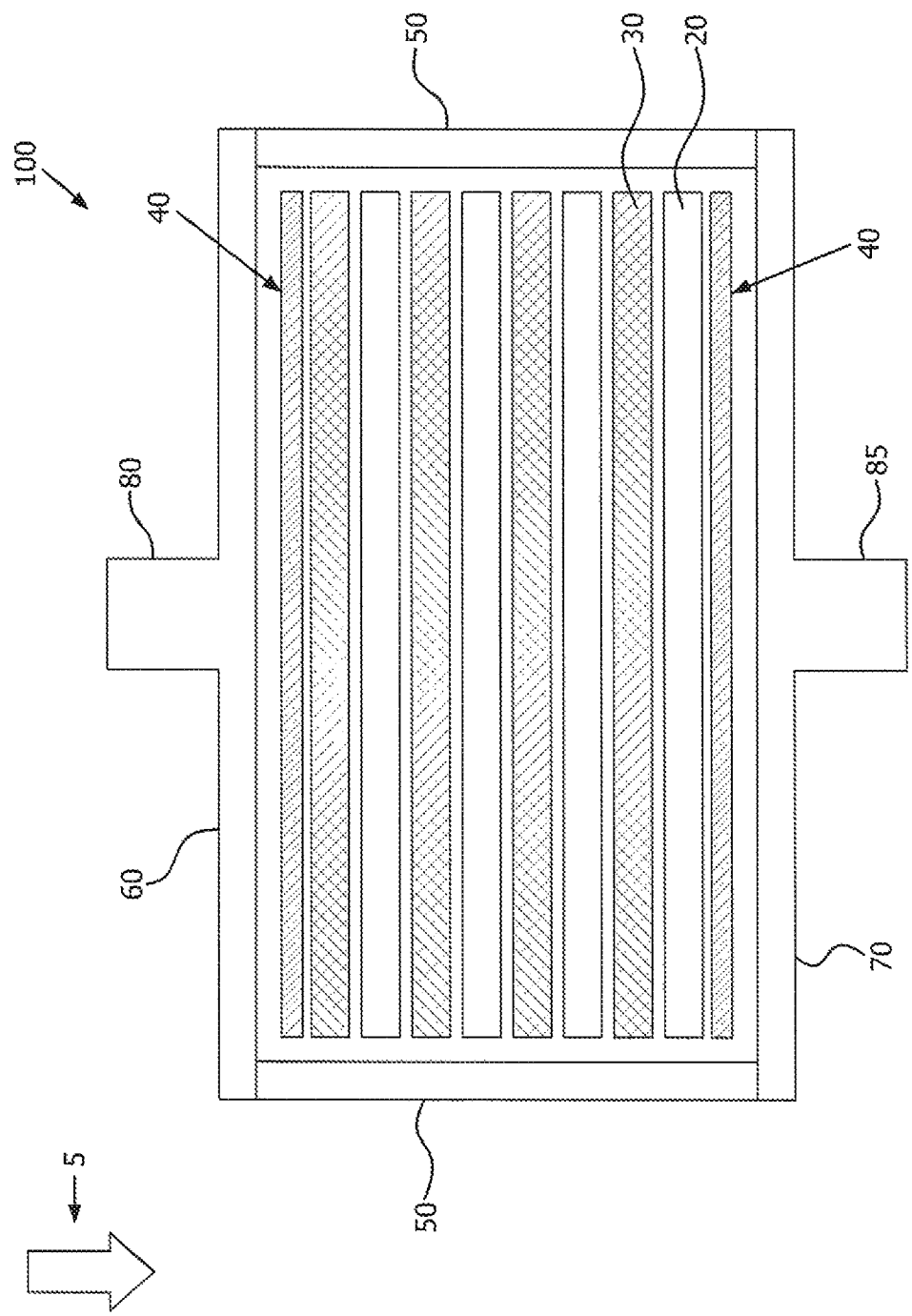
FIG. 5 is a schematic illustration of a cross-section of a chromatography device containing a stacked membrane assembly according to an exemplary embodiment.

Turning to FIGS. 4 and 5, the stacked membrane assembly 10 may be disposed within a housing 50 having a first flow distributor 60 and a second flow distributor 70 disposed at opposite ends of the housing 50. In exemplary embodiments, the housing 50 is cylindrical. In one embodiment, the flow distributor 60 contains an impingement surface so that the flow of the aqueous mixture is redirected 90 degrees from the feed direction. This redirection prevents the flow from directly impinging on the polymer membrane and promotes a more uniform flow front. The polymer membranes in the stacked membrane assembly 10 may be adhered to the housing 50 at the inner walls of the housing via any conventional process (e.g., melt sealing or use of a sealant) that prevents flow between the membrane periphery and the housing. The flow distributors 60, 70 may be sealed to the housing 50 by a similar or identical process. Each flow distributor 60, 70 includes an inlet 80 and an outlet 85, respectively, to permit the flow of an aqueous mixture through the affinity chromatography device 100. Specifically, the inlet 80 permits fluid flow into the housing 50 and the outlet 85 permits fluid flow out of the housing 50. In use, the aqueous mixture flows sequentially through the polymer membranes in the stacked membrane assembly 10 in the direction illustrated by arrow 5. As the aqueous mixture is passed through the chromatography device 100, the affinity ligand reversibly binds to the targeted protein or antibody, thereby effectively removing it from the aqueous mixture. The targeted protein or antibody may be removed from the affinity ligand, for example, by passing a fluid that has a lower pH through the device.

In a further embodiment, at least one polymer membrane having inorganic particles therein (such as the polymer membrane(s) described above) is wrapped around a perforated hollow or solid core 150 to form a wound membrane assembly 110. In one exemplary embodiment depicted generally in FIG. 6, the membrane assembly 110 contains a polymer membrane 20 that includes first inorganic particles having a first nominal particle size and second inorganic particles having a second nominal particle size. The first and second inorganic particles may be of the same type (e.g., porous silica) or may be of different types (e.g., silica and zeolite), and may have the same or different nominal particle size(s). The mixture of inorganic particles within the polymer membrane 20 may be any mixture, such as, for example, a 50/50 blend, a 30/70 blend, a 60/40 blend, a 25/75, or a 20/80 blend.

In some embodiments, an intermediate film is positioned on the polymer membrane and is wrapped with the polymer membrane such that upon winding, the intermediate film is situated between the wound layers of the polymer membrane. The intermediate film may be a fluoropolymer film or a non-fluoropolymer film (e.g., a polypropylene or other polyolefin film). Additionally, the intermediate film may be porous or non-porous.

In another embodiment, the membrane assembly 110 may be formed of a single polymer membrane 20 containing therein inorganic particles having a single nominal particle size. For example, a single polymer membrane that is at least partially filled with inorganic particles with a nominal particle size and having an affinity ligand bonded thereto may be used as a membrane assembly 110. Additionally, multiple polymer membranes having therein inorganic particles of the same particle size may be used to form the membrane assembly 110.

Figure 7:
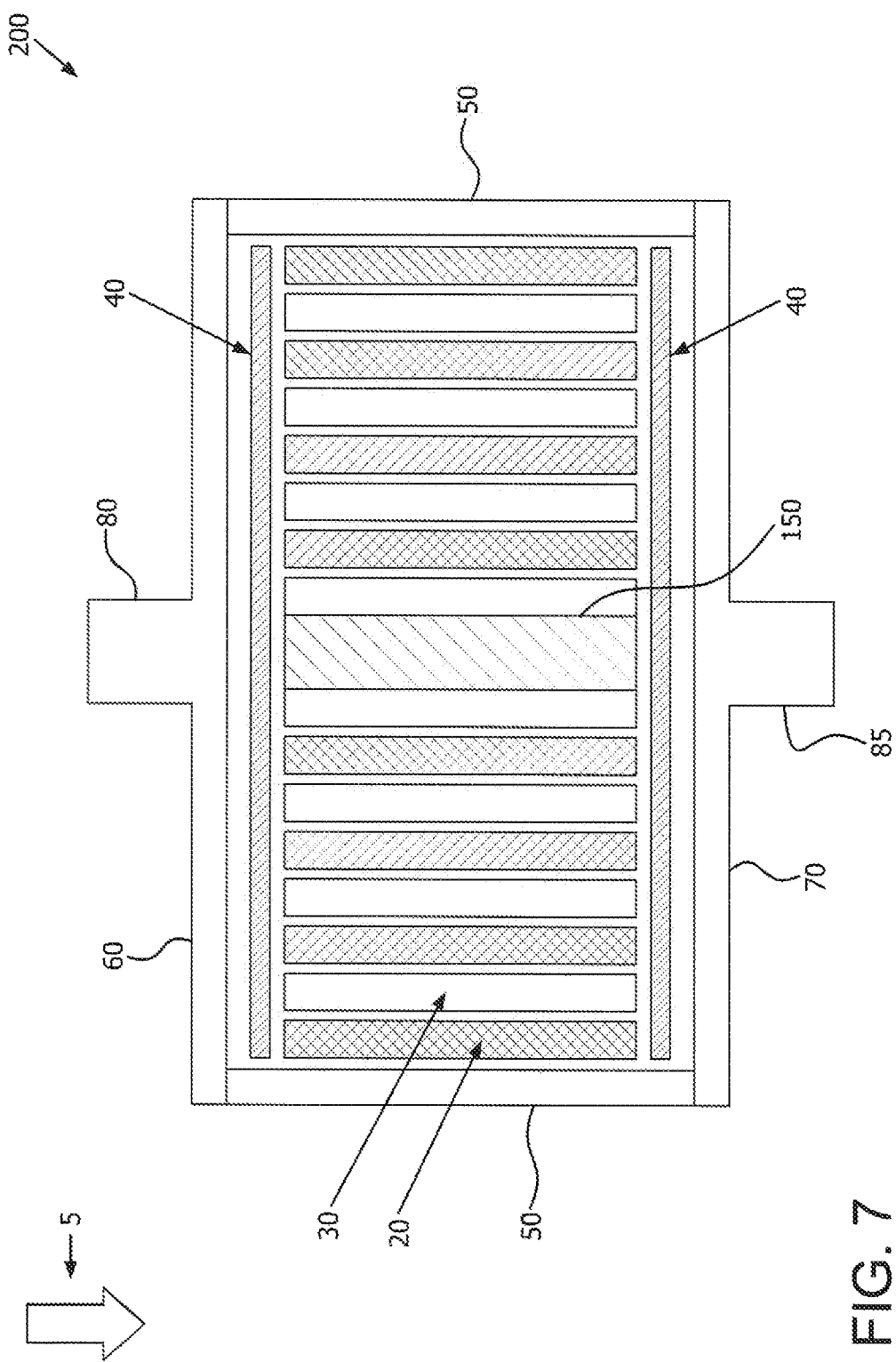
FIG. 7 is a schematic illustration of a cross-section of a chromatography device containing a wound membrane assembly having two polymer membranes in an alternating configuration in accordance with an embodiment.
Figure 8:
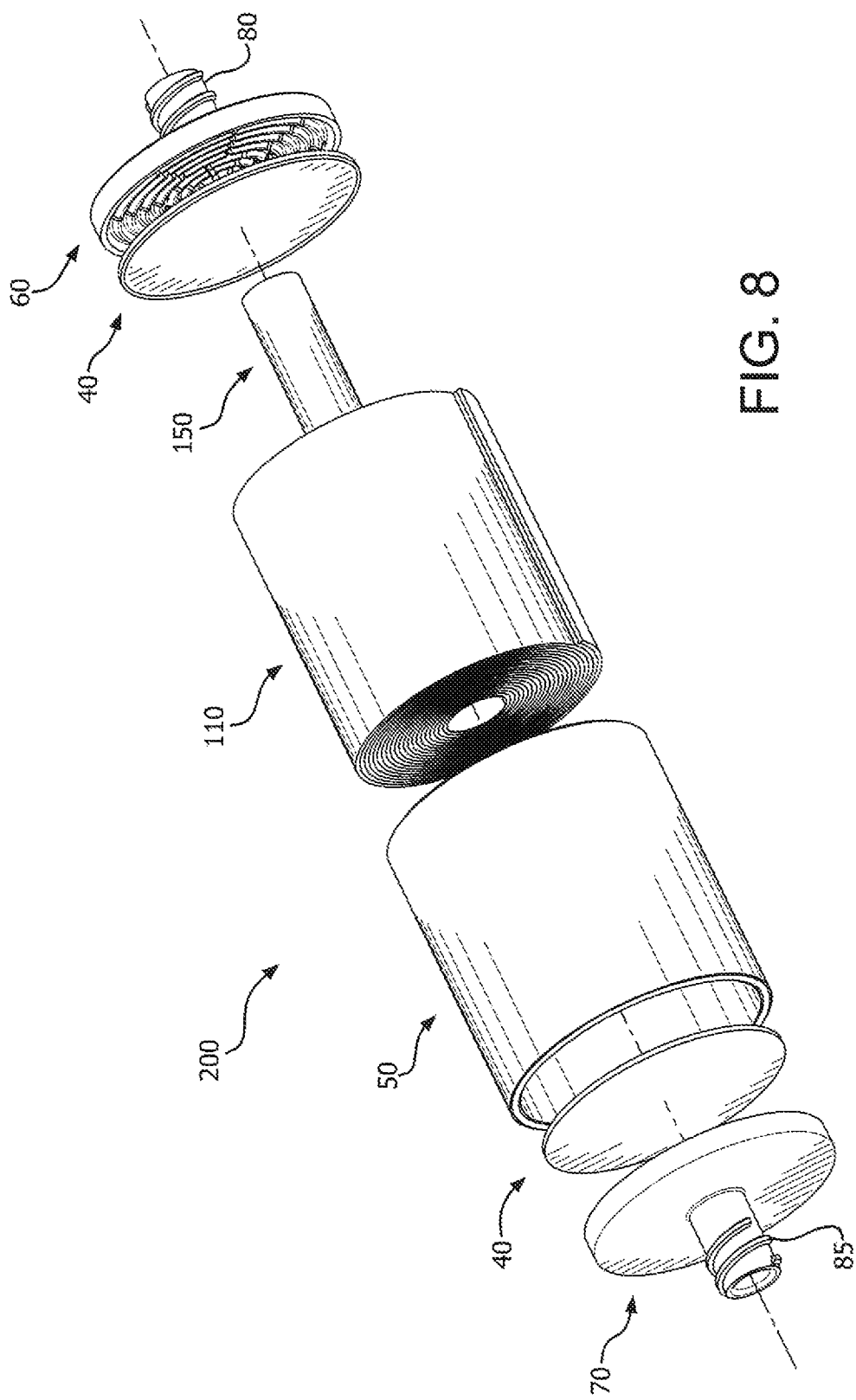
FIG. 8 is an exploded view of a chromatography device containing a spirally wound membrane assembly in accordance with exemplary embodiments.

Two (or more) polymer membranes may be present in the wound membrane assembly 110. When more than one polymer membrane is present in the wound membrane assembly 110, a first polymer membrane 20 having a first nominal particle size and a second polymer membrane 30 having a second nominal polymer size may be layered on each other in a stacked configuration and then wound about the core 150 in the stacked configuration to form the wound membrane assembly 110, such as is depicted in FIG. 7. Alternatively, a first polymer membrane 20 may be wound around the core 150 and then a second polymer membrane 30 may be subsequently wrapped around the wound first polymer membrane 110. It is to be appreciated that if greater than two membranes is desired, the polymer membranes 20, 30 may be stacked in an alternating or non-alternating configuration as discussed above prior to winding.

Figure 6:
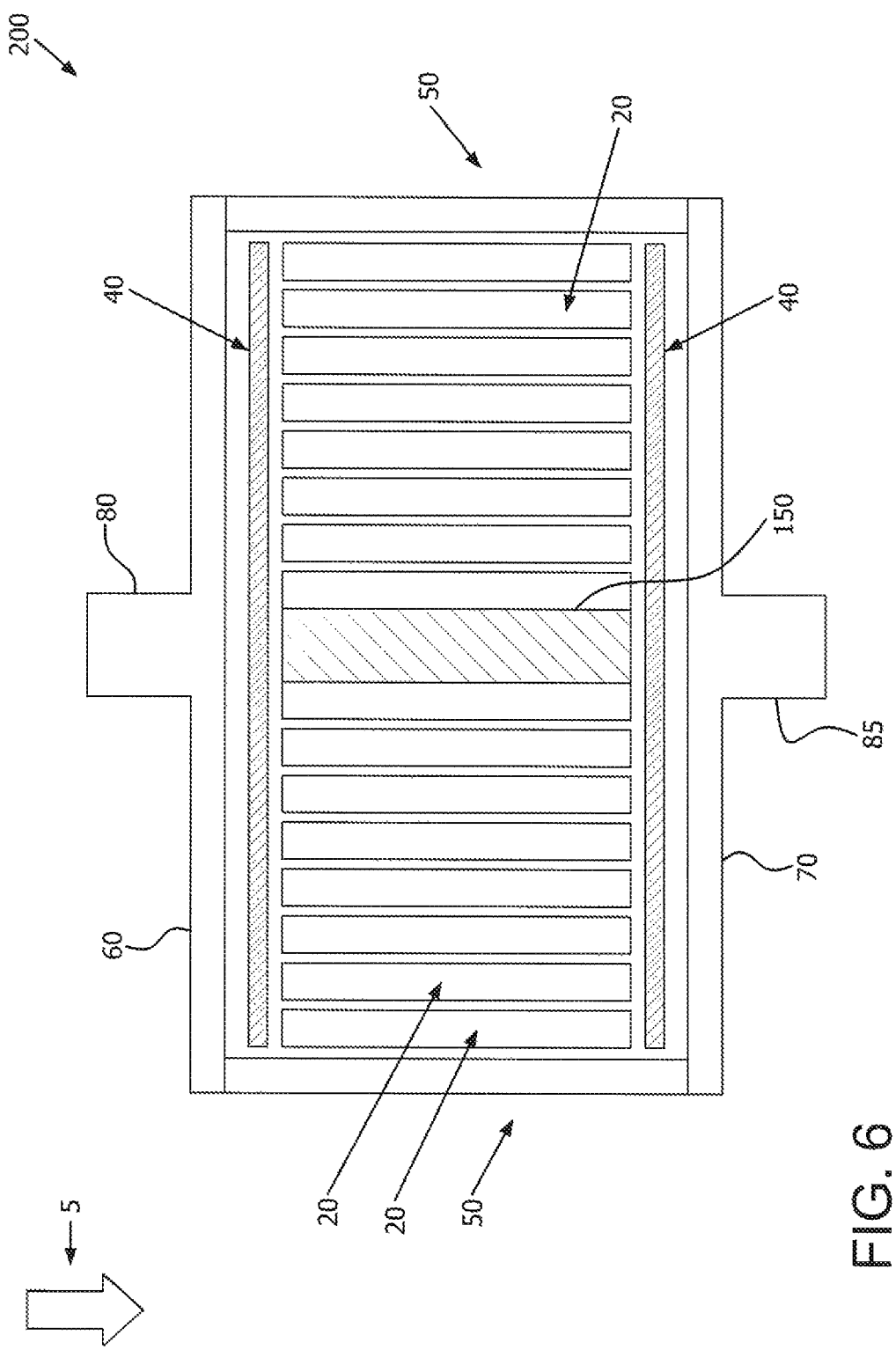
FIG. 6 is a schematic illustration of a cross-section of a chromatography device containing a wound membrane assembly having a polymer membrane in accordance with an embodiment.

As depicted in FIGS. 6 and 7, the wound membrane assembly 110 is disposed within a housing 50 having a first flow distributor 60 and a second flow distributor 70 disposed at opposite ends of the housing 50 The chromatography device 200 includes an inlet 80 and an outlet 85 to permit the flow of an aqueous mixture through the affinity chromatography device 100. Specifically, the inlet 80 permits fluid flow into the housing 50 and the outlet 85 permits fluid flow out of the housing 50. In exemplary embodiments, the housing is cylindrical. The wound membrane assembly 110 may further include at least one porous frit 40 positioned normal to the wound membrane assembly 110 and adjacent to flow distributor 60 and/or flow distributor 70. In one embodiment, the core 150 is solid and the flow distributor 60 contains an impingement surface so that the flow of the aqueous mixture is redirected radially from the feed direction. In use, the aqueous mixture flows through the polymer membrane(s) in the membrane assembly 110 in the direction illustrated by arrow 5, orthogonal to the areal thickness direction of the membrane. As the aqueous mixture is passed through the chromatography device 200, the affinity ligand reversibly binds to the targeted protein or antibody, thereby effectively removing it from the aqueous mixture. The targeted protein or antibody may be removed from the affinity ligand, for example, by passing a fluid that has a lower pH through the device.

In an alternate embodiment, the core 150 is a hollow, porous core that enables the aqueous mixture to flow outwardly from the core 150 and through the polymer membrane(s). Alternatively, the aqueous mixture flows through the polymer membrane(s) inwardly and into the core 150.

Figure 9A:
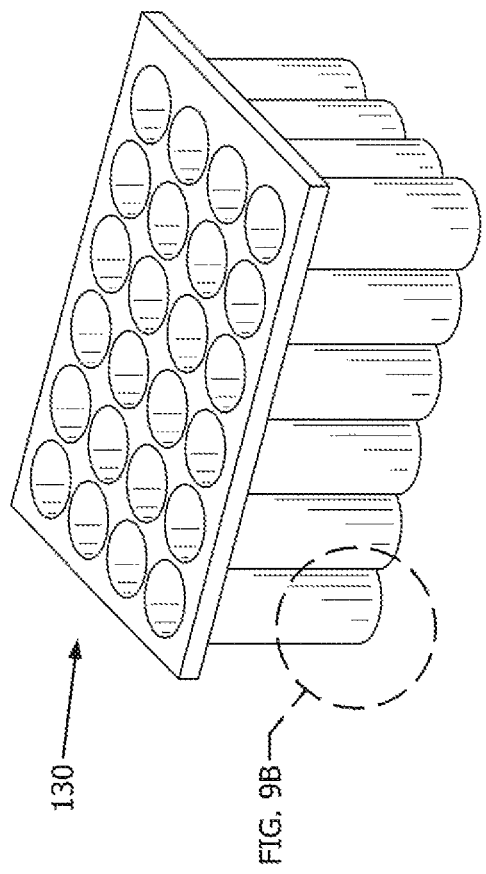
FIG. 9A is a schematic illustration of a multi-well plate in accordance with an embodiment of the invention.
Figure 9B:
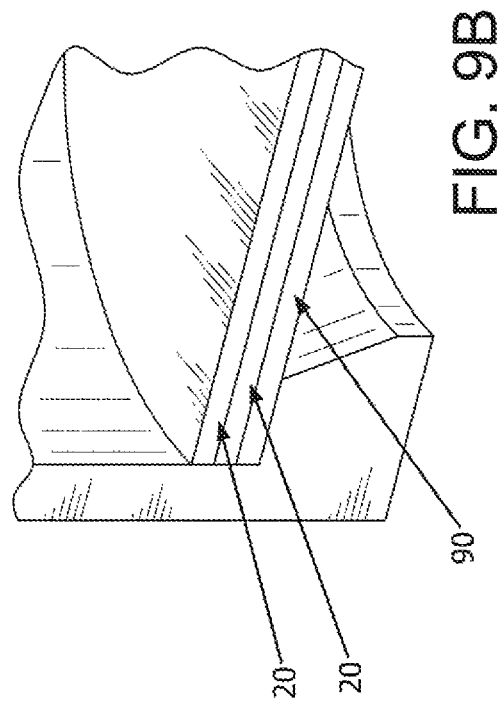
FIG. 9B is a schematic illustration of a portion of the multi-well plate depicted in FIG. 9A showing a portion of a stacked membrane assembly positioned on a porous substrate according to at least one exemplary embodiment.

In yet another embodiment, a polymer membrane, a multilayer stacked membrane assembly, or a spiral wound membrane assembly as described above may be affixed to a multi-well plate 130 containing a porous surface 90 separating a lower chamber that can be operated at reduced pressure from an upper chamber that is operated at a higher (e.g., atmospheric) pressure. In the embodiment depicted in FIGS. 9A and 9B, the membrane assembly contains a plurality of polymer membranes 20 having therein first inorganic particles having a first nominal particle size and second inorganic particles having a second nominal particle size. In operation, the aqueous mixture flows normal to the polymer membranes 20.

The affinity chromatography devices described herein have a dynamic binding capacity (DBC) of at least 30 mg/ml at 10% breakthrough at a residence time of 20 seconds or less where an Fc binding protein is the affinity ligand. Where an antibody, a non-Fc binding protein, or a polysaccharide is the affinity ligand, the chromatography devices have a dynamic binding capacity (DBC) of at least 0.07 micromol/ml at 10% breakthrough at a residence time of 20 seconds or less. In addition, the chromatography devices may be used multiple times without losing substantial dynamic binding capacity. Specifically, the chromatography devices may be cleaned with a caustic solution (e.g. sodium hydroxide) after each separation process and reused.

Although exemplary embodiments of the membrane assemblies 10, 110 are described herein, it is to be appreciated that any number of polymer membranes as well as any and all combinations of types of polymer membranes, types of inorganic particles, sizes of inorganic particles, shapes of inorganic particles, and orientations of the polymer membranes within the membrane assembly are within the scope of this disclosure. Also, some or all of the polymer membranes may vary in composition, thickness, permeability, etc. from each other.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

Test Methods

It should be understood that although certain methods and equipment are described below, other methods or equipment determined suitable by one of ordinary skill in the art may be alternatively utilized.

Method for Determining the Dynamic Binding Capacity at 10% Breakthrough

Figure 10:
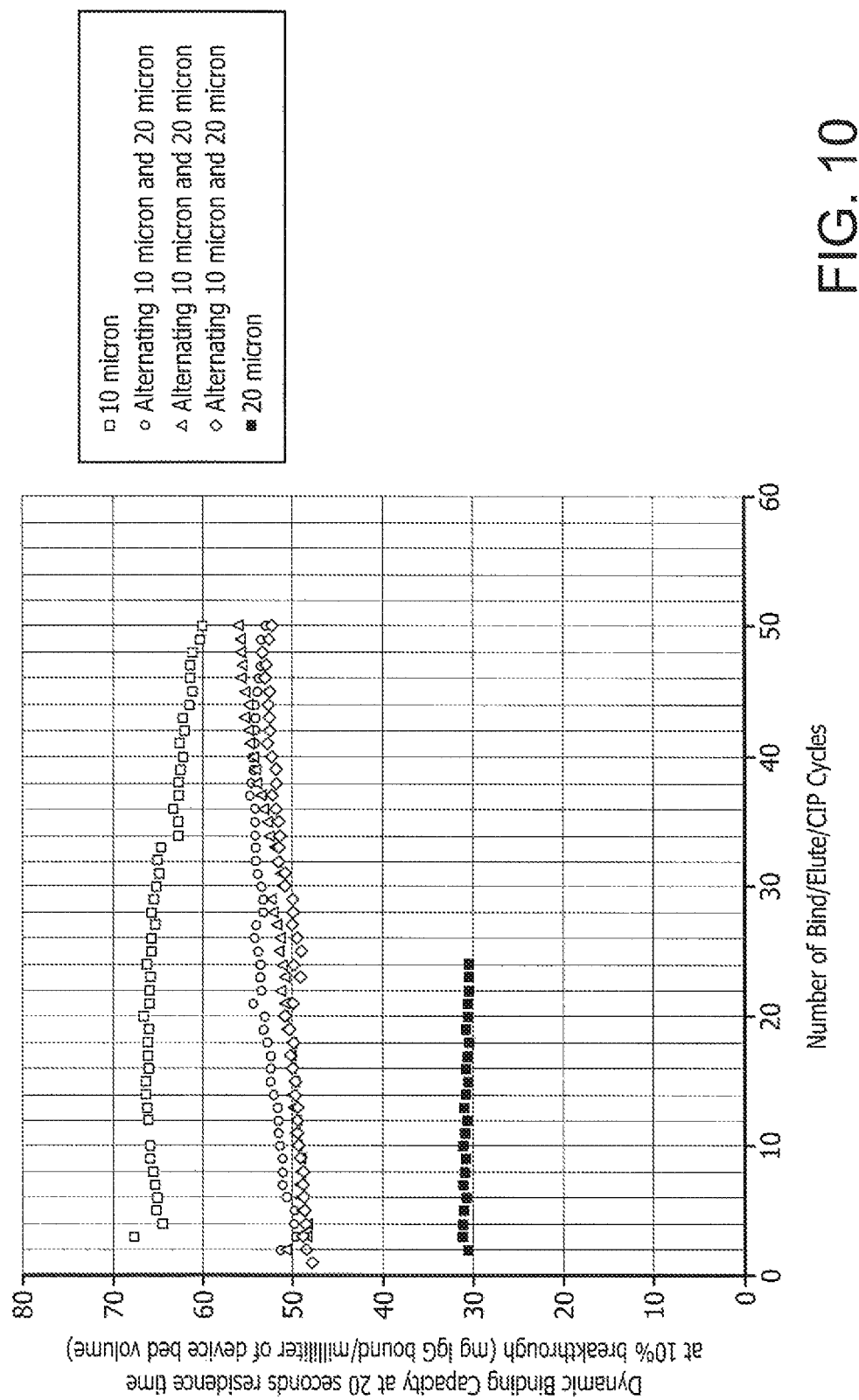
FIG. 10 is a graphical illustration of the dynamic binding capacity (DBC) at twenty (20) second residence time at 10% breakthrough (milligrams IgG bound per milliliter bed volume) of various chromatography devices.

The chromatography device was inserted in a AKTApurifier™ (GE Healthcare) liquid chromatography system's flow path and a single cycle consisting of the following protocol was performed multiple times to generate the data shown in FIG. 10. For the purpose of examining caustic solutions and their effect on dynamic binding capacity, only a caustic clean in place (CIP) solution was used. Table 1 sets forth the solutions utilized. Table 2 sets forth the protocol steps to determine the dynamic binding capacity at 10% breakthrough.

TABLE 1

| Solution | Description |
|---|---|
| A | 50 mM Phosphate supplemented with 150 mM Sodium Chloride, pH ~7.4 |
| B | 100 mM Citrate, pH ~3.5 |
| CIP | 0.1M NaOH |
| Feed | 1.2-1.3 mg/mL polyclonal IgG (Lee Biosciences) dissolved in Solution A |
| Storage | 20/80 v/v ethanol/water |

TABLE 2

| Step | Solution | Volume of Solution Used (Number of Bed Volumes) | Bed Volume/ Volumetric Flow Rate = Seconds Residence Time |
|---|---|---|---|
| 1 | A | 6 | 20 |
| 2 | B | 6 | 20 |
| 3 | A | 6 | 20 |
| 4 | Feed | Until Absorbance at 280 nm = 10% Breathrough | 20 |
| 5 | A | 3 | 20 |
| 6 | B | 10 | 20 |
| 7 | A | 3 | 20 |
| 8 | CIP | 15 minutes contact time at 1 mL/min | N/A |
| 9 | A | 6 | 20 |
| 10 | Water | 6 | 20 |
| 11 | Storage | 6 | 20 |
| 12 | Return to Step 1 and continue in this manner until the desired number of cycles is executed. | | |

The dynamic binding capacity was determined for the above-described chromatography devices in this manner. The dynamic binding capacity of the commercial devices were determined by the same method, but with the following exception: The residence time for the commercial devices was 60 seconds instead of 20 seconds.

Thus, the chromatography devices described herein were evaluated at threefold faster volumetric flow rates than the commercial devices were evaluated, with the exception of the CIP steps, which were identical.

EXAMPLES

Example 1—Stacked Membranes

A porous polytetrafluoroethylene (PTFE) membrane having 15 mass percent PTFE and 85 mass percent porous silica particles (Grace, Baltimore, Md.) having a nominal particle size of 10 micron (Grace, Baltimore, Md.) was obtained. Additionally, a porous PTFE membrane having 15 mass percent PTFE and 85 mass percent porous silica particles (Grace, Baltimore, Md.) having a nominal particle size of 20 micron was obtained. The porous silica particles in the PTFE membranes were substantially the same with respect to other chemical and physical characteristics such as chemical composition, particle shape, nominal particle porosity, nominal particle pore dimensions, and nominal particle BET surface areas.

Table 3 lists some of the physical characteristics of the two porous PTFE membranes.

TABLE 3

| Porous Membrane | Mass Percent Porous Silica Particles | Mass Percent PTFE | Porous Silica Nominal Particle Size (micron) | Nominal Porous Membrane Thickness (micron) | Porous Membrane Density (grams/cc) | Gurley Number (sec) | Nominal Porous Silica Pore Size (nm) |
|---|---|---|---|---|---|---|---|
| A | 85 | 15 | 10 | 650 | 0.41 | 30 | 100 |
| B | 85 | 15 | 20 | 650 | 0.42 | 15 | 100 |

Porous membranes A and B were used to manufacture affinity chromatography devices. A polypropylene flow distributor was affixed to one end of a polypropylene cylinder housing. A porous polypropylene frit was placed in the housing. The desired number of PTFE membrane layers were stacked on the polypropylene frit within the housing. (See Table 4). A second porous polypropylene frit was placed on top of the PTFE membrane stack. A second polypropylene flow distributor was affixed to the end of the cylindrical housing opposite the first polypropylene flow distributor. The chromatography device was sealed via a heating process.

TABLE 4

| Device Designation | Porous Membrane Used | Membrane Thickness Orientation with Respect to Fluid Flow Direction During Characterization | Bed Volume (mL) | Intermediate Device Permeability, $k \times 10^{-12}$ $cm^2$ |
|---|---|---|---|---|
| C | 10 layers of membrane A | Same | 3.4 | 133 |
| D | 5 layers of membrane A and 5 layers of membrane B | Same | 3.5 | 182 |
| E | 5 layers of membrane A and 5 layers of membrane B | Same | 3.5 | 195 |
| F | 5 layers of membrane A and 5 layers of membrane B | Same | 3.5 | 201 |
| G | 10 layers of membrane B | Same | 3.5 | 301 |

The intermediate devices were then treated in the same manner as the device of Example 3 and as a result, Protein A was covalently bonded to the stacked PTFE membranes (e.g., membrane assembly).

The affinity chromatography devices whose manufacture was described above were tested to evaluate their twenty (20) second residence time dynamic binding capacities using multiple cycles and using the protocol described in the Test Methods set forth herein. The performance of each of these affinity chromatography devices is shown in FIG. 10.

Figure 11:
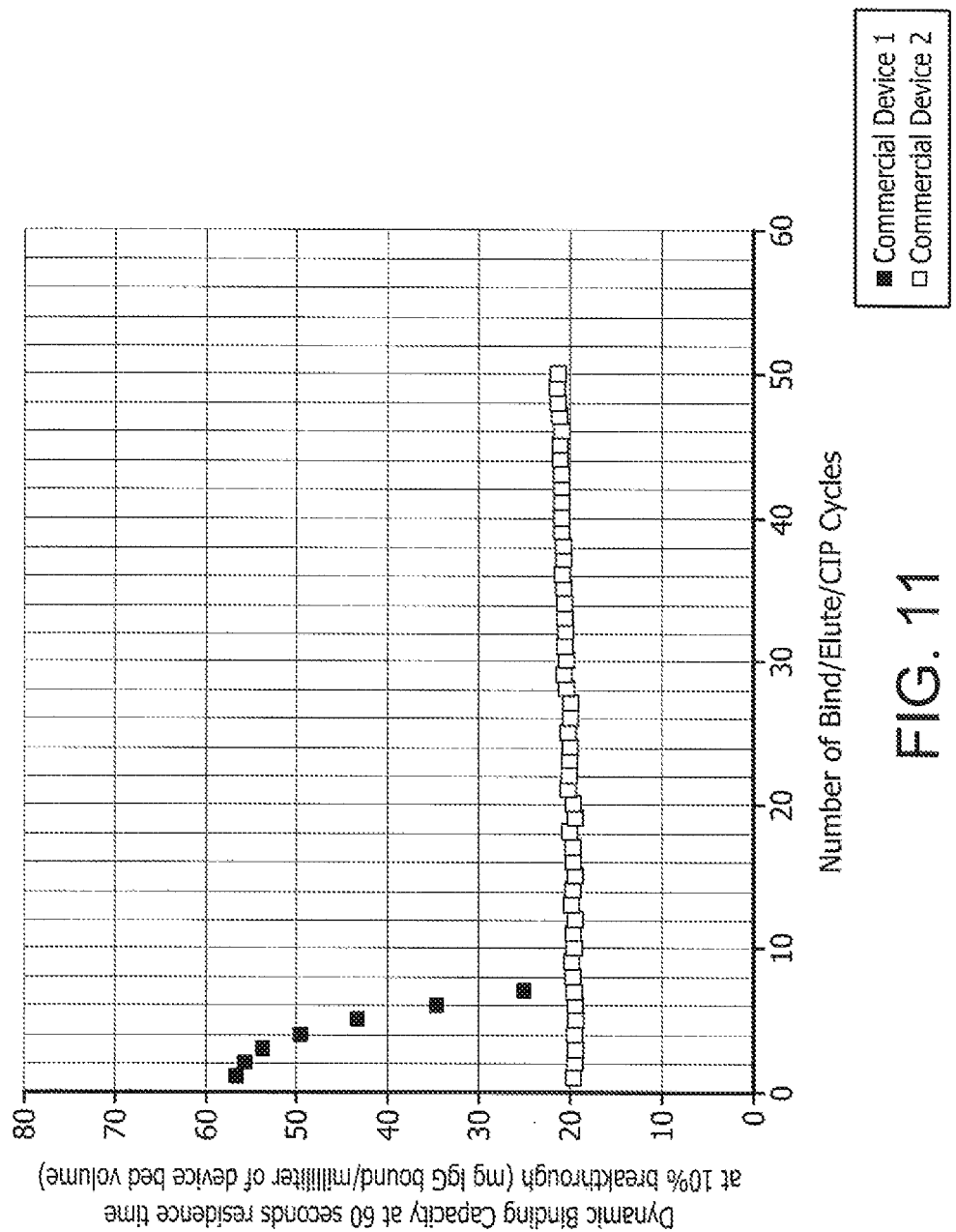
FIG. 11 is a graphical illustration of the dynamic binding capacity (DBC) at sixty (60) second residence time at 10% breakthrough (milligrams IgG bound per milliliter bed volume) of two comparative chromatography devices.

Two different commercial packed particle bed affinity chromatography devices were obtained and tested in the same manner, with the exception that they were evaluated at a sixty (60) seconds residence time. One of the commercial devices was packed with silica particles containing residual boron (Commercial Device 1) and the other commercial device was packed with agarose (Commercial Device 2). The performance of the two commercial affinity chromatography devices is depicted in FIG. 11. The affinity chromatography devices were evaluated at threefold faster rates than the commercial affinity chromatography devices.

Example 2—Spiral Wound Membrane

Porous PTFE Membrane B from Example 1 was used to construct a spiral wound affinity chromatographic device. A length of PTFE Membrane B was wound about a solid core with a lathe and membrane tensioning member until the diameter of the resulting wound membrane assembly was slightly greater than the inner diameter of a cylindrical polypropylene housing. The wound membrane assembly was then cut to the desired length dimension with a cutting tool while the wound device assembly was rotating on the lathe. The wound membrane assembly was inserted within a properly dimensioned cylindrical polypropylene housing after the housing had been split down its length to enable insertion of the wound membrane assembly. Porous polypropylene frits and polypropylene distributors were assembled at the opposing ends of the cylindrical housing. The device was sealed via a heating process.

Three sealed intermediate chromatography devices of 3.5 mL bed volume were manufactured in this manner. These devices were constructed using the same polypropylene distributors and polypropylene frits that were used in Example 1. The intermediate devices were then treated in the same manner as the device of Example 3 and, as a result, Protein A was covalently bonded to the wound membrane assembly.

It was discovered that when a test solution (water) flowed through these chromatography devices at various volumetric flow rates, the permeability of the wound membrane assembly was substantially greater than the permeability of the stacked membrane assembly of Example 1. In the devices containing the wound membrane assembly, the test solution flowed orthogonal to the areal thickness direction of the membrane.

Example 3

This example illustrates one method for covalently binding Protein A to a porous PTFE membrane or multiple porous PTFE membranes that include PTFE and porous silica particles, where the porous membrane or multiple porous membranes was (were) integrated into a device housing having an inlet and an outlet for flowing fluids. Although this method is described with respect to an affinity chromatography device that contains a stacked membrane assembly, it is to be appreciated that this method is applicable regardless of the orientation or configuration of the porous membrane relative to the fluid flow path and regardless of the particle shape, nominal particle size, nominal particle pore size or nominal particle pore volume of the porous silica particle phase, and whether the membrane assembly is stacked or wound or otherwise assembled.

All solutions were 0.2 micron filtered unless stated otherwise. In addition, all solutions were flowed through the devices with the aid of a syringe pump or a peristaltic pump.

A 3.5 mL bed volume chromatography device was manufactured from a porous polytetrafluoroethylene (PTFE) membrane having 15 mass % PTFE and 85 mass % porous silica particles (Davisil® Silica Unbonded Grades, XWP1000A, 16-24 µm, Grace, Baltimore, Md.). A stacked membrane assembly was produced. The membrane assembly was washed with 21 mL of a solution of 95 parts by volume ethanol (Sigma-Aldrich, St. Louis, Mo.) and 5 parts by volume deionized water (Neu-Ion, Inc., Baltimore, Md.) at a volumetric flow rate of 0.7 mL/min. Next, 10.5 mL of a non-filtered solution of 5.885 grams of 3-glycidoxypropyltrimethoxy silane (G6720, UCT Specialties, LLC, Bartram, Pa.) were dissolved in 94.5 mL of a solution of 95 parts by volume ethanol and 5 parts by volume deionized water and flowed through the membrane assembly at a volumetric flow rate of 0.7 mL/min. The device was left standing for about seventeen hours at room temperature. Then the device was heated to 90° C. and held at that temperature for two hours, followed by cooling the device to room temperature for one hour, after which, the membrane assembly was washed with 21 mL of a solution of 95 parts by volume ethanol and 5 parts by volume deionized water at a volumetric flow rate of 0.7 mL/min.

The membrane assembly was then treated with a solution of sulfuric acid and deionized water, pH=0.8, by flowing 21 mL of the solution through the device assembly at a volumetric flow rate of 0.7 mL/min, followed by heating at 90 degrees centigrade for two hours and then cooling the device to room temperature for one hour, followed by washing the treated membrane with 42 mL of 10 mM acetate buffer, pH=4.2. The 10 mM acetate buffer, pH=4.2 was prepared by combining 3,952 mL of deionized water with 40 mL of 1M acetic acid (Sigma-Aldrich, Saint Louis, Mo.) and 8 mL of 1M sodium hydroxide (Sigma-Aldrich, Saint Louis, Mo.). Then, 120 mL of 10 mM acetate buffer was combined with 6.417 grams of sodium periodate (Sigma-Aldrich, Saint Louis, Mo.) and 10.5 mL of this solution was flowed through the membrane assembly at 0.7 mL/min. The device was then left to react for ninety minutes at room temperature, followed by flowing through the membrane assembly, 21 mL of 10 mM acetate buffer, pH-=4.2. This was followed by flowing through the membrane assembly, 21 mL of a 0.01M sodium carbonate buffer, pH=10.9 at a volumetric flow rate of 0.7 mL/min. The 0.01M sodium carbonate buffer, pH=10.9, was prepared by combining 1000 mL of deionized water with 1.06 grams of sodium carbonate (Sigma-Aldrich, Saint Louis, Mo.) and 5.84 grams of sodium chloride (EMD Chemicals, Inc., Gibbstown, N.J.).

Next, 21 mL of a 4 mg/mL solution of Protein A was flowed through the device in a recirculating flow pattern at a volumetric flow rate of 0.7 mL/min for about 17 hours at room temperature. 4 mg/mL solution of Protein A was prepared by combining 202.4 mL of the pH=10.9 sodium carbonate buffer prepared earlier and 17.6 mL of a 50 mg/mL Protein A solution (Repligen rSPA, Waltham, Mass.). After about 17 hours, the Protein A solution recirculation process was stopped and the recirculated solution's absorbance at 280 nm was measured and compared to that of the freshly prepared 4 mg/mL Protein A solution.

The membrane assembly was then washed at a volumetric flow rate of 0.7 mL/min with 21 mL of a second 0.01M sodium carbonate buffer, pH=10.5, which had been prepared by combining 1000 mL of deionized water, 1.06 grams sodium carbonate and 58.4 grams sodium chloride. This was followed by another wash step using 21 mL of 0.01M sodium carbonate buffer, pH=10.9 at a volumetric flow rate of 0.7 mL/min. Then, 31.5 mL of a 1 mg/mL sodium borohydride (Sigma-Aldrich, Saint Louis, Mo.) solution in 0.01M sodium carbonate buffer was flowed through the membrane assembly at a volumetric flow rate of 0.26 mL/min. This was followed by flowing through the membrane assembly 31.5 mL of a 0.05 M phosphate buffer solution, pH=7.4, at a volumetric flow rate of 0.7 mL/min. The 0.05 M phosphate buffer solution, pH=7.4, had been prepared earlier by combining 1000 mL of deionized water with 1.035 grams of sodium phosphate monobasic monohydrate (Sigma-Aldrich, Saint Louis, Mo.), 11.393 grams of sodium phosphate dibasic heptahydrate (Sigma-Aldrich, Saint Louis, Mo.) and 8.766 grams of sodium chloride. The membrane assembly was then washed with 21 mL of deionized water at a volumetric flow rate of 0.7 mL/min. Next, the membrane assembly was washed with 21 mL of a solution of 20 parts by volume ethanol and 80 parts by volume deionized water. The device was then equipped with inlet and outlet caps and stored at 4° C. to 8° C.

Example 4

This example illustrates a second method for covalently binding Protein A to a porous PTFE membrane or multiple porous PTFE membranes that include PTFE and porous silica particles, where the porous membrane or multiple porous membranes was (were) integrated into a device housing having an inlet and an outlet for flowing fluids. Although this method is described with respect to an affinity chromatography device that contains a stacked membrane assembly, it is to be appreciated that this method is applicable regardless of the orientation or configuration of the porous membrane relative to the fluid flow path and regardless of the particle shape, nominal particle size, nominal particle pore size or nominal particle pore volume of the porous silica particle phase, and whether the membrane assembly is stacked or wound or otherwise assembled.

This method is different from the method described in Example 3 in the following aspects. An aldehyde silane (PSX1050, UCT Specialties, LLC, Bartram, Pa.) was used instead of the epoxy silane of Example 3 A number of other manufacturing steps were eliminated, as will be apparent to those skilled in the art, upon comparison of this method and the method of Example 3.

All solutions were 0.2 micron filtered unless stated otherwise. All solutions were flowed through the devices with the aid of a syringe pump or a peristaltic pump.

A 3.5 mL bed volume chromatography device was manufactured from a porous membrane sheet including polytetrafluoroethylene (PTFE) (15 mass percent) and porous silica particles (85 mass percent) having a nominal particle size of 20 microns (Davisil® Silica Unbonded Grades, XWP1000A, 16-24 µm, Grace, Baltimore, Md.). A stacked membrane assembly was produced. The membrane assembly was washed with 21 mL of a solution of 95 parts by volume ethanol (Sigma-Aldrich, St. Louis, Mo.) and 5 parts by volume deionized water (Neu-Ion, Inc., Baltimore, Md.) at a volumetric flow rate of 0.7 mL/min. 10.5 mL of an unfiltered solution of 3.21 grams of aldehyde silane (PSX1050, UCT Specialties, LLC, Bartram, Pa.) dissolved in 97.0 mL of a solution of 95 parts by volume ethanol and 5 parts by volume deionized water was flowed through the membrane assembly at a volumetric flow rate of 0.7 mL/min. The device was left standing for about seventeen hours at room temperature. Then the device was heated to 90° C. and held at that temperature for two hours, followed by cooling the device to room temperature for one hour, after which, the membrane assembly was washed with 42 mL of a solution of 95 parts by volume ethanol and 5 parts by volume deionized water at a volumetric flow rate of 0.7 mL/min. The membrane assembly was then washed with 21 mL of a 0.01M sodium carbonate buffer, pH=10.9 at a volumetric flow rate of 0.7 mL/min. The 0.01M sodium carbonate buffer, pH=10.9, was prepared by combining 1000 mL of deionized water with 1.06 grams of sodium carbonate (Sigma-Aldrich, Saint Louis, Mo.) and 5.84 grams of sodium chloride (EMD Chemicals, Inc., Gibbstown, N.J.).

Next, 21 mL of a 4 mg/mL solution of Protein A was flowed through the device in a recirculating flow pattern at a volumetric flow rate of 0.7 mL/min for about 17 hours at room temperature. The 4 mg/mL solution of Protein A was prepared by combining 202.4 mL of the pH=10.9 sodium carbonate buffer prepared earlier and 17.6 mL of a 50 mg/mL Protein A solution (Repligen rSPA, Waltham, Mass.). After about 17 hours, the Protein A solution recirculation process was stopped and the recirculated solution's absorbance at 280 nm was measured and compared to that of the freshly prepared 4 mg/mL Protein A solution.

The membrane assembly was then washed at a volumetric flow rate of 0.7 mL/min with 21 mL of a second 0.01M sodium carbonate buffer, pH=10.5, which had been prepared by combining 1000 mL of deionized water, 1.06 grams sodium carbonate and 58.4 grams sodium chloride. This washing was followed by a wash step using 21 mL of 0.01M sodium carbonate buffer, pH=10.9 at a volumetric flow rate of 0.7 mL/min. Then 31.5 mL of a 1 mg/mL sodium borohydride (Sigma-Aldrich, Saint Louis, Mo.) solution in 0.01M sodium carbonate buffer was flowed through the device membrane assembly at a volumetric flow rate of 0.26 mL/min. This was followed by flowing through the device membrane assembly 31.5 mL of a 0.05 M phosphate buffer solution, pH=7.4, at a volumetric flow rate of 0.7 mL/min. The 0.05 M phosphate buffer solution, pH=7.4, had been prepared earlier by combining 1000 mL of deionized water with 1.035 grams of sodium phosphate monobasic monohydrate (Sigma-Aldrich, Saint Louis, Mo.), 11.393 grams of sodium phosphate dibasic heptahydrate (Sigma-Aldrich, Saint Louis, Mo.) and 8.766 grams of sodium chloride. Then the device membrane assembly was washed with 21 mL of deionized water at a volumetric flow rate of 0.7 mL/min. Then the device membrane assembly was washed with 21 mL of a solution of 20 parts by volume ethanol and 80 parts by volume deionized water. The device was then equipped with inlet and outlet caps and stored at 4° C. to 8° C.

The device prepared as described in this example was evaluated with polyclonal IgG for one cycle and then it was evaluated with a crude Chinese Hamster Ovary (CHO) cell clarified culture medium (Aragen, Morgan Hills, Calif.) including a monoclonal antibody and impurities such as host cell proteins. It was demonstrated that the device of this example was useful for purifying monoclonal antibodies from a crude CHO cell clarified culture medium.

Example 5—Stacked Membrane Device Including Porous Silica Mixture

A porous polytetrafluoroethylene (PTFE) membrane having 85 mass percent porous silica particles (Davisil® Silica Unbonded Grades, XWP1000A, 16-24 μm, Grace, Baltimore, Md.) and 15 mass percent PTFE was obtained. The porous silica particles were present as a 50/50 by mass mixture of two different nominal particle sizes and these corresponded to the porous silicas used to produce porous membranes A and B in Example 1.

Table 5 lists some of the physical characteristics of the membrane obtained.

TABLE 5

| Porous membrane | Mass percent porous silica particles | Mass percent PTFE | Porous silica nominal particle sizes (micron) | Nominal porous membrane thickness (micron) | Porous membrane density (grams/cc) | Gurley Number (sec) | Nominal porous silica pore size (nm) |
|---|---|---|---|---|---|---|---|
| C | 85 | 15 | 10 & 20 | 650 | 0.42 | 10 | 100 |

Porous PTFE membrane C was used to manufacture an affinity chromatography device. A polypropylene flow distributor was affixed to one end of a polypropylene cylinder housing. A porous polypropylene frit was placed in the housing. The desired number of PTFE membrane layers were stacked on the polypropylene frit within the housing. (See Table 6). A second porous polypropylene frit was placed on top of the PTFE membrane stack. A second polypropylene flow distributor was affixed to the end of the cylindrical housing opposite the first polypropylene flow distributor. The chromatography device was sealed via a heating process.

TABLE 6

| Device Designation | Porous membrane used | Membrane thickness orientation with respect to fluid flow direction during characterization | Bed Volume (mL) | Intermediate device permeability, k × 10$^{-12}$ cm$^2$ |
|---|---|---|---|---|
| 10499664 | 12 layers of membrane C | Same | 3.6 | 303 |

The intermediate device was then treated in the same manner as the device of Example 3 and as a result, Protein A was covalently bonded to the membrane assembly.

The affinity chromatography device was then tested to evaluate its 10% dynamic binding capacity at twenty (20) second residence time using the protocol described in Test Methods set forth herein. It was determined that the affinity chromatography device had a 10% dynamic binding capacity of 44 mg IgG per mL bed volume at 20 seconds residence time.

Example 6—Spiral Wound Membrane Device Including Porous Silica Mixture

Porous PTFE Membrane C from Example 5 was used to construct a spiral wound affinity chromatographic device. A length of PTFE Membrane C was wound about a solid core with a lathe and membrane tensioning member until the diameter of the wound membrane assembly was slightly greater than the inner diameter of a polypropylene housing. The wound membrane assembly was then cut to the desired length with a cutting tool while the wound device assembly was rotating on the lathe. The desired dimensioned wound membrane assembly was inserted within a properly dimensioned cylindrical polypropylene housing after the housing had been split down its length to enable insertion of the wound membrane assembly. Porous polypropylene frits and polypropylene distributors were assembled at the opposing ends of the cylindrical housing. The device was sealed via a heating process thereby producing an intermediate chromatography device of 3.5 mL bed volume.

The intermediate device was then treated in the same manner as the device of Example 3 and, as a result, Protein A was covalently bonded to the wound membrane assembly. It was discovered that when a test solution (water) flowed through the affinity chromatography device at various volumetric flow rates, the permeability of the wound membrane assembly was about twice the permeability of the stacked membrane assembly of Example 5. In the device containing the wound membrane assembly, the test solution flowed orthogonal to the areal thickness direction of the membrane. The affinity chromatography device had a 10% dynamic binding capacity of 31 mg IgG per mL bed volume at 20 seconds residence time.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An affinity chromatography device comprising:
   a housing;
   an inlet configured to permit fluid flow into the housing;
   first and second flow distributors, the first flow distributor and the second flow distributor positioned at opposing ends of the housing;
   an outlet configured to configured to permit fluid flow out of the housing; and
   a stacked membrane assembly disposed within the housing, the stacked membrane assembly comprising two or more polytetrafluoroethylene membranes containing therein first inorganic particles having a first nominal particle size and second inorganic particles having a second nominal particle size,
   wherein at least one of: the first inorganic particles, the second inorganic particles, or any combination thereof has covalently bonded thereto affinity ligands comprising Fc binding proteins, that reversibly bind to a targeted protein or antibody, and
   wherein the affinity chromatography device is configured to provide:
   a dynamic binding capacity of at least 30 mg/ml at 10% breakthrough; and
   a residence time of 20 seconds or less.
2. The affinity chromatography device of claim 1, wherein the first and second inorganic particles are chosen from silica particles, zeolite particles, hydroxyapatite particles, metal oxide particles or any combination thereof.

3. The affinity chromatography device of claim 1, wherein the two or more polytetrafluoroethylene membranes are expanded polytetrafluoroethylene membranes.

4. The affinity chromatography device of claim 1, wherein the affinity ligands are chosen from Protein A, Protein G, Protein L, human Fc receptor protein, antibodies, polysaccharides, or any combination thereof.

5. The affinity chromatography device of claim 1, wherein the first nominal particle size and the second nominal particle size are chosen from 0.1 microns, 0.5 microns, 1 micron, 5 microns, 10 microns, 15 microns, 20 microns, 25 microns, or any combination thereof.

6. The affinity chromatography device of claim 1, wherein the first nominal particle size is different from the second nominal particle size.

7. The affinity chromatography device of claim 1, wherein the first and second inorganic particles are of the same particle type.

8. An affinity chromatography device comprising:
a housing;
an inlet configured to permit fluid flow into the housing;
first and second flow distributors, the first flow distributor and the second flow distributor positioned at opposing ends of the housing;
an outlet configured to permit fluid flow out of the housing, and
a stacked membrane assembly disposed within the housing, the stacked membrane assembly comprising two or more polytetrafluoroethylene membranes containing therein inorganic particles of the same type having a nominal particle size,
wherein the inorganic particles have covalently bonded thereto affinity ligands comprising Fc binding proteins, that reversibly bind to a targeted protein or antibody, and
wherein the affinity chromatography device is configured to provide:
a dynamic binding capacity of at least 30 mg/ml at 10% breakthrough and;
a residence time of 20 seconds or less.

9. The affinity chromatography device of claim 8, wherein the nominal particle size is chosen from 0.1 microns, 0.5 microns, 1 micron, 5 microns, 10 microns, 15 microns, 20 microns, or 25 microns.

10. The affinity chromatography device of claim 8, wherein the two or more polytetrafluoroethylene membranes are expanded polytetrafluoroethylene membranes.

11. The affinity chromatography device of claim 8, wherein the inorganic particles are chosen from silica particles, zeolite particles, hydroxyapatite particles, metal oxide particles, or any combination thereof.

12. The affinity chromatography device of claim 8, wherein the affinity ligands are chosen from Protein A, Protein G, Protein L, human Fc receptor protein, antibodies that specifically bind to other proteins, polysaccharides, or any combination thereof.

13. The affinity chromatography device of claim 8, wherein the inorganic particles are first inorganic particles having a first nominal particle size, and wherein each of the at least two polytetrafluoroethylene membranes further comprise second inorganic particles having a second nominal particle size.

14. The affinity chromatography device of claim 8, wherein the second inorganic particles have covalently bonded thereto affinity ligands that reversibly bind to a targeted protein or antibody.

15. The affinity chromatography device of claim 8, wherein the first and second inorganic particles are chosen from: silica particles, zeolite particles, hydroxyapatite particles, metal oxide particles, or any combination thereof.

16. The affinity chromatography device of claim 8, wherein the affinity ligands are chosen from: Protein A, Protein G, Protein L, human Fc receptor protein, antibodies, polysaccharides, or any combination thereof.

17. The affinity chromatography device of claim 13, wherein the first nominal particle size and the second nominal particle size are chosen from: 0.1 microns, 0.5 microns, 1 micron, 5 microns, 10 microns, 15 microns, 20 microns, 25 microns, or any combination thereof.

18. The affinity chromatography device of claim 13, wherein the first nominal particle size is different from the second nominal particle size.

19. The affinity chromatography device of claim 8, wherein the first and second inorganic particles are of the same particle type.

* * * * *